United States Patent [19]

Takematsu et al.

[11] 4,319,915

[45] Mar. 16, 1982

[54] HERBICIDAL COMPOSITIONS

[75] Inventors: Tetsuo Takematsu, Utsunomiya; Hideshi Tsuchiya, Tokyo, both of Japan

[73] Assignees: Mitsubishi Gas Chemical Co., Inc.; Japan Hydrazine, both of Tokyo, Japan

[21] Appl. No.: 150,223

[22] Filed: May 12, 1980

[30] Foreign Application Priority Data

May 16, 1979 [JP] Japan ................................ 54-59886

[51] Int. Cl.[3] ..................... A01N 43/54; A01N 43/58

[52] U.S. Cl. ....................................................... 71/92

[58] Field of Search ........................................... 71/92

[56] References Cited

U.S. PATENT DOCUMENTS

| | | | |
|---|---|---|---|
| 2,614,916 | 10/1952 | Hoffmann et al. | 71/92 |
| 3,235,363 | 2/1966 | Luckenbaugh et al. | 71/92 |
| 4,150,966 | 4/1979 | Tsuchiya et al. | 71/92 |

OTHER PUBLICATIONS

Povolotskaya et al. Chem. Abst. vol. 55 (1961) 1822b.

*Primary Examiner*—Catherine L. Mills

*Attorney, Agent, or Firm*—Abelman, Frayne, & Rezac

[57] ABSTRACT

Herbicidal compositions comprising as active ingredients maleio hydroazide and a substituted methyl uracil.

1 Claim, No Drawings

HERBICIDAL COMPOSITIONS

This invention relates to herbicidal compositions containing as their active ingredients uracil type herbicides and maleic acid hydrazide. Uracil type herbicides containing uracil compounds such as 5-bromo-3-sec-butyl-6-methyluracil (hereinafter called "bromacil"), 3-cyclohexyl-5,6-trimethyleneuracil (hereinafter called "lenacil"), 5-bromo-3-isopropyl-6-methyluracil (hereinafter called "isocil") or 5-chloro-3-tert-butyl-6-methyluracil (hereinafter called "terbacil") have excellent herbicidal effects on annual weeds such as crab-grass, goose-grass, common purslane, asiatic dayflower and cleavers, biennial weeds such as green foxtail, water foxtail and annual blue grass, and perennial weeds of small size such as common mugwort, kalimeris and field horsetail.

Usually, however, it was necessary to use the uracil type herbicides in an amount of 0.8 to 2.4 kg per 10 a. in order to give full play to herbicidal effects of these herbicides on perennial weeds of large size which grow in non-farming lands such as factory premises, vacant lands, railroad trucks, or roads. (The abbreviation, "a.", as used herein means as areal unit, "are", which is equivalent to 100 $m^2$ that is 1/100 hectares.) Furthermore, these herbicides failed to bring about the desired effect to the full on creepers such as pueraria, cayratia and india mockstrawberry even when they are used in large amounts. In addition thereto, the uracil type herbicides had such drawbacks that they pollute soil when they come to be present therein because they are extremely stable and difficultly decomposable in soil, and that they are quite slow of displaying their herbicidal effects. Maleic acid hydrazide (hereinafter called "MH") and its salts, on the other hand, have heretofore been used for controlling perennial weeds. However, the amount of MH used was 300 to 2,000 g/10 a. even in the case where the portions of the weeds appearing above the soil were cut after about one week lapse subsequently to the MH treatment in a spring to summer season during which the weeds grow rankly.

However, since weeds belonging to family Gramineae, such as common reed, needle-grass and Japanese plume-grass, are strongly resistant to herbicides, herbicidal effects obtainable by separately applying thereto of choline salt of maleic acid hydrazide or bromacil are insufficient even when said choline salt or bromacil is used in large amounts. For instance, even in the case where choline salt of MH is used in an amount greater than 5 kg per 10 a., the effect obtainable thereby merely remains to suppress the growth of weeds, and in order to expect the perfect control it is necessary that the choline salt is sprayed over the weed at the period of from late in June to early in July, said period being a nutriment translocation period of the weeds, and further that at the 5th to 7th day after the spraying of the choline salt, the stalk and leaf portions of the weeds are cut down. In the case of bromacil where it is intended to be used for the purpose of preventing an asphalt pavement from being broken through by means of the weeds growing upwards, the amount of bromacil required for the purpose is more than 4 kg per 10 a. and, in addition thereto, there is need to use in admixture therewith DPA (2,2-dichloropropionic acid sodium salt) herbicide in the same amount as in the bromacil.

As the result of various researches extensively conducted by the present inventors on a process for improving the prior art involving the above-mentioned drawbacks indelibly associated with uracil type herbicides and MH, respectively, they have finally accomplished the present invention on the basis of their finding that the use of the uracil type herbicides in combination with MH, even when their respective amounts used are quite small, can result in an excellent herbicidal effect on perennial weeds which were heretofore difficultly controllable.

Uracil type compounds as referred to in the present invention are intended to designate compounds represented by chemical structural formulas, respectively, as mentioned below.

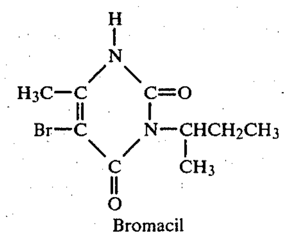

Bromacil

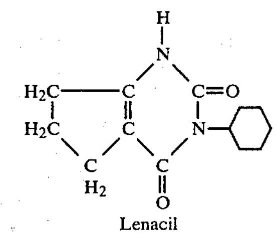

Lenacil

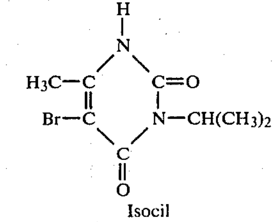

Isocil

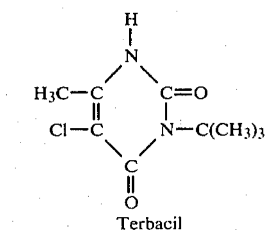

Terbacil

By maleic acid hydrazide or its salt as used in the present invention is meant to include maleic acid hydrazide, choline salt of maleic acid hydrazide, diethanolamine salt of maleic acid hydrazide, sodium salt of maleic acid hydrazide or potassium salt of maleic acid hydrazide.

By virtue of application to various weeds of the present herbicidal compositions, there can be controlled, for example, annual or biennial weeds such as crab-grass, goose-grass, green foxtail, canada fleabane, annual fleabane, hogweed, persicaria, bog stitchwort, common chickweed, umbrella sedge, water foxtail, asiatic dayflower, chenopodium, cleavers, annual blue grass, barnyard grass and common purslane, and perennial weeds such as common reed, needle-grass, Japanese plume-grass, kalimeris, dandelion, field horsetail, europian woodrorrel, swamp foxtail, nutgrass, tall golden-rod, common mugwort, dock weeds yellow cress, ixeris, cayratia, pueraria and false nettle. The present herbicidal compositions have strong herbicidal effects on perennial creeper weeds such as pueraria, india mock-strawberry and cow vetch.

In the herbicidal compositions of the present invention when they are intended to be actually used, the uracil type herbicide or herbicides to be present therein generally in an amount of 10 to 300 g/10 a., preferably 20 to 200 g/10 a. When the amount of the uracil type herbicide or herbicides contained in the present compositions is less than 10 g/1 a., the expected herbicidal effect obtainable thereby becomes small and, on the other hand, the use of said herbicide or herbicides in larger amounts exceeding 300 g/10 a. is not preferable because the amount thereof that remains unutilized under the soil proportionally increases. In case where the weeds which have already grown up enough are intended to be treated with the present herbicidal compositions, it is preferably from the standpoint of efficiency to use the present uracil type herbicide or herbicides in tolerably larger amounts but falling within the above-mentioned ranges.

The amount of MH to be present in the present herbicidal compositions which are intended to be used is generally 150 to 1,000 g/10 a., preferably 200 to 800 g/10 a., calculated as maleic acid hydrazide.

The proportion of the uracil type compounds to MH in the present herbicidal compositions can be arbitrarily decided in such a manner that the amount of the former may range from 20 to 300 g/10 a. and that of the latter may range from 150 to 1,000 g/10 a. when the compositions containing these two ingredients are actually applied to the weeds. Preparation of the two ingredients used in the proper proportion as specified above in the usual way results in a herbicidal composition having an excellent herbicidal effect. In a herbicidal composition of the present invention, the content of the uracil type compound usually is 0.5 to 5% by weight, preferably 1–4% by weight, while the content of MH is 5 to 30% by weight, while the content of MH is 5 to 30% by weight, preferably 10–20% by weight. Of the uracil type compounds used in the present invention, which all have excellent herbicidal effects, most preferred is bromacil as it exhibits particularly excellent effect. As MH, choline salt of maleic acid hydrazide having particularly excellent effect is preferred, followed by ethanolamine salt of maleic acid hydrazide.

Generally, the herbicidal compositions of the present invention are prepared in the form of liquid or dust preparation, and the liquid preparation is particularly preferred from the stand point of efficiency. The herbicidal composition of the invention is usually used in the amount of 1 kg/10 a. to 5 kg/10 a., depending on the types of weeds to be controlled and the contents of the uracil type compound and MH used.

From the standpoint of uniform spraying and efficiency, it is preferable that the present herbicidal composition is used after diluting the same in an amount corresponding to that necessary for 10 a. with about 100 liters of water. The present herbicidal compositions containing the uracil type herbicides and MH exhibit quick and excellent herbicidal effects even when respective amounts of these two ingredients are quite smaller than those of the ingredients when they are intended to be used independently.

The process for the preparation of herbicidal compositions according to the present invention is illustrated below with reference to examples.

EXAMPLE 1

To a mixture comprising 70 parts by weight of an aqueous solution (containing 30% by weight of maleic acid hydrazide) of choline salt of maleic acid hydrazide and 20 parts by weight of an aqueous bromacil solution (containing 20% by weight of bromacil) were added 5 parts by weight of a surface active agent and 5 parts by weight of water. The resultant mixture was thoroughly stirred to obtain a herbicidal composition. The thus obtained composition (hereinafter called "composition 1") was found to contain 20% by weight of maleic acid hydrazide and 4% by weight of bromacil.

EXAMPLE 2

To a mixture comprising 70 parts by weight of an aqueous solution (containing 30% by weight of maleic acid hydrazide) and 10 parts by weight of an aqueous bromacil solution (containing 20% by weight of bromacil) were added 5 parts by weight of a surface active agent and 15 parts by weight of water. The resultant mixture was thoroughly stirred to obtain a herbicidal composition. The thus obtained composition (hereinafter called "composition 2") was found to contain 20% by weight of maleic acid hydrazide and 2% by weight of bromacil.

Test examples are given below to demonstrate the effects of the herbicidal compositions of the present invention.

Test Example 1

Into each of porcelain pots of 10 cm in inside diameter was transplanted water foxtail (height 15 cm; 4 tillerings), which is a plant being considered as an indication of biennial weeds belonging to family Gramineae. After having taken root, the transplanted weed was sprayed over its stalks and leaves with a predetermined amount of the composition 1, which has been diluted with 100 liters of water before application thereof. The weed thus treated was allowed to stand, as it was, for one month without cutting down the stalks and leaves thereof one week after the treatment, including also the case where bromacil or MH was applied alone to the weed. The herbicidal effect of each case was investigated by visual observation to obtain the results as shown in Table 1, wherein the amount used was represented in terms of the amount of each herbicide to be used per 10 a.

TABLE 1

| Amount used (g) | | | Herbicidal |
|---|---|---|---|
| Composition 1 | Bromacil | MH | effect |
| — | 50 | — | 0 |
| — | 500 | — | 2 |
| — | 800 | — | 4 |
| — | — | 500 | 0* |
| 2,000 | (80) | (400) | 5 |
| 1,000 | (40) | (200) | 4 |
| Not treated | — | — | 0 |

In Table 1, the herbicidal effect was evaluated in terms of a mark of 0 to 5 and an asterisk, respectively, the meanings of which were as follows:

| | |
|---|---|
| 0 | Weed grown soundly. |

-continued

| | |
|---|---|
| 1 | 20% of weed withered to death. |
| 2 | 40% of weed withered to death. |
| 3 | 60% of weed withered to death. |
| 4 | 80% pf weed withered to death. |
| 5 | Weed completely withered to death. |
| * | Growth of weed was suppressed to some extent. |

Test Example 2

Into each of unglazed flowerpots of 20 cm in inside diameter filled with farm land soil was transplanted a tuber (250 g) of sweet potato, which is a plant being considered as an indication of perennial weeds. Thereafter, at the time when new stalks and leaves sprouted and grown to a length of 20 cm, the stalks and leaves were sprayed with the composition 2 in a concentration as attained by dilution with 100 liters of water. One month after the treatment, herbicidal effect of the composition 2, as well as bromacil and MH used singly, was investigated to obtain the results as shown in Table 2, wherein the amount used was represented in terms of the amount of each herbicide to be used per 10 a.

TABLE 2

| Amount used (g) | | | Herbicidal |
|---|---|---|---|
| Composition 2 | Bromacil | MH | effect |
| — | 100 | — | 0 |
| — | — | 500 | 0* |
| 1,000 | (20) | (200) | 4 |
| 2,000 | (40) | (400) | 5 |
| 3,000 | (60) | (600) | 5 |
| Not treated | — | — | 0 |

In Table 2, the herbicidal effect was evaluated in terms of a mark of 0 to 5 and an asterisk, respectively, the meanings of which were as follows:

| | |
|---|---|
| 0 | Stalks and leaves of sweet potato grown soundly. |
| 1 | 20% of stalks and leaves of sweet potato withered to death. |
| 2 | 40% of stalks and leaves of sweet potato withered to death. |
| 3 | 60% of stalks and leaves of sweet potato withered to death. |
| 4 | 80% of stalks and leaves of sweet potato withered to death. |
| 5 | 100% of stalks and leaves of sweet potato withered to death. |
| * | Growth inhibition to some extent was observed. |

EXAMPLE 3

To a mixture comprising 34 parts by weight of an aqueous solution (containing 30% by weight of maleic acid hydrazide) of choline salt of maleic acid hydrazide and 20 parts by weight of an aqueous bromacil solution (containing 20% by weight of bromacil) were added 5 parts by weight of a surface active agent and 5 parts by weight of water. The resultant mixture was thoroughly stirred to obtain a herbicidal composition. The thus obtained composition (hereinafter called "composition 3") was found to contain 10% by weight of maleic acid hydrazide and 4% by weight of bromacil.

EXAMPLE 4

To a mixture comprising 70 parts by weight of an aqueous solution (containing 30% by weight of maleic acid hydrazide) and 5 parts by weight of an aqueous bromacil solution (containing 20% by weight of bromacil) were added 5 parts by weight of a surface active agent and 20 parts by weight of water. The resultant mixture was thoroughly stirred to obtain a herbicidal composition. The thus obtained composition (hereinafter called "composition 4") was found to contain 20% by weight of maleic acid hydrazide and 1% by weight of bromacil.

Test Example 3

In the field where weeds were growing thick, there were provided test plots of 2 m×1 m each, and stalks and leaves of the weeds in each plot were sprayed with a predetermined amount of the composition 2 in a concentration as attained by dilution with 100 liters (per 10 a.) of water. Heights of the weeds were 40 cm in common mugwort, 70 cm in quack grass, 50 cm in dock weed, 40 cm in shepherd's purse, 60 cm in crab-grass and 50 cm in cayratia. One month after the treatment, herbicidal effect of the composition 2, including bromacil and MH used singly, was investigated to obtain the results as shown in Table 3, wherein the amount used was represented in terms of the amount of each herbicide to be used per 10 a.

In this test example as well as Test Example 4 subsequent thereto, the herbicidal effect was evaluated in terms of a mark of 0 to 5 and an asterisk, respectively, the meanings of which were as follows:

TABLE 3

| Amount used (g) | | | Herbicidal effect | | | | | |
|---|---|---|---|---|---|---|---|---|
| Composition 2 | Bromacil | MH | Common mugwort | Quack grass | Dock weed | Shepherd's purse | Crab-grass | Cayratia |
| — | 50 | — | 3 | 3 | 2.5 | 3 | 3.5 | 3 |
| — | — | 500 | 0* | 0* | 0* | 0* | 0* | 0* |
| 2,500 | (50) | (500) | 5 | 5 | 5 | 5 | 5 | 5 |
| Not | — | — | 0 | 0 | 0 | 0 | 0 | 0 |

TABLE 3-continued

| Amount used (g) | | | Herbicidal effect | | | | | |
|---|---|---|---|---|---|---|---|---|
| Composition 2 | Bromacil | MH | Common mugwort | Quack grass | Dock weed | Shepherd's purse | Crabgrass | Cayratia |
| treated. | | | | | | | | |

0 Weed grown soundly.
0.5 10% of weed withered to death.
1 20% of weed withered to death.
1.5 30% of weed withered to death.
2.0 40% of weed withered to death.
2.5 50% of weed withered to death.
3.0 60% of weed withered to death.
3.5 70% of weed withered to death.
4.0 80% of weed withered to death.
4.5 90% of weed withered to death.
5.0 100% of weed withered to death.*Growth inhibition of weed to some extent was observed.

Test Example 4

Japanese plume-grasses (1.5 m in height) growing in the field were sprayed by means of a sprayer over their stalks and leaves with the compositions 1, 2, 3 and 4, respectively, each having been diluted with 100 liters of water. One month and three months, respectively, after the treatment, herbicidal effect of each compositions, including bromacil and MH used singly, was investigated to obtain the results as shown in Table 4, wherein the amount used was represented in terms of the amount of each herbicide to be used per 10 a.

TABLE 4

| Herbicide | Amount used (g) | Amount of ingredient (g) Bromacil | MH | Herbicidal effect After one month | After three months |
|---|---|---|---|---|---|
| Bromacil | 50 | 50 | — | 0 | 0 |
| Bromacil | 100 | 100 | — | 1.5 | 0 |
| Bromacil | 200 | 200 | — | 1.5–2 | 0 |
| MH | 500 | — | 500 | 1.5 | 0 |
| MH | 1,000 | — | 1,000 | 2 | 0 |
| Composition 1 | 5,000 | (200) | (1,000) | 4.5–5 | 5 |
| Composition 2 | 5,000 | (100) | (1,000) | 4–4.5 | 5 |
| Composition 4 | 5,000 | (50) | (1,000) | 3 | 4.5 |
| Composition 3 | 5,000 | (200) | (500) | 4.5–5 | 4 |
| Composition 1 | 2,500 | (100) | (500) | 4–4.5 | 3.5 |
| Composition 2 | 2,500 | (50) | (500) | 2.5 | 3.5–4 |
| Not treated | — | — | — | 0 | 0 |

What we claim is:

1. A herbicidal composition which comprises as its active ingredients at least one uracil compound selected from the group consisting of 5-bromo-3-sec-butyl-6-methyluracil, 3-cyclohexyl-5,6-trimethyleneuracil, 5-bromo-3-isopropyl-6-methyluracil and 5-chloro-3-tert-butyl-6-methyluracil, and maleic acid hydrazide or its salt wherein the uracil type compound is in amount of 1 to 4% by weight and the maleic acid hydrazide or its salt is in amount of 10 to 20% by weight, all percentages being based on the weight of said composition.

* * * * *